(12) United States Patent
Fan et al.

(10) Patent No.: US 10,888,231 B2
(45) Date of Patent: Jan. 12, 2021

(54) AUTOMATIC INTRAORAL 3D SCANNER WITH LOW COHERENCE RANGING

(71) Applicant: Carestream Dental Technology Topco Limited, London (GB)

(72) Inventors: Chuanmao Fan, Rochester, NY (US); Victor C. Wong, Pittsford, NY (US); Yiyi Guan, Pittsford, NY (US); Jean-Marc Inglese, Bussy-Saint-Georges (FR); Edward R. Shellard, Atlanta, GA (US)

(*) Notice: Subject to any disclaimer, the term of this patent is extended or adjusted under 35 U.S.C. 154(b) by 0 days.

(21) Appl. No.: 16/324,824

(22) PCT Filed: Aug. 10, 2016

(86) PCT No.: PCT/US2016/046224
§ 371 (c)(1),
(2) Date: Feb. 11, 2019

(87) PCT Pub. No.: WO2018/031003
PCT Pub. Date: Feb. 15, 2018

(65) Prior Publication Data
US 2019/0223732 A1    Jul. 25, 2019

(51) Int. Cl.
*A61B 5/00* (2006.01)
*A61C 9/00* (2006.01)
*A61B 1/247* (2006.01)

(52) U.S. Cl.
CPC .......... *A61B 5/0088* (2013.01); *A61B 5/0066* (2013.01); *A61B 5/0073* (2013.01); *A61B 5/682* (2013.01); *A61C 9/0073* (2013.01); *A61B 1/247* (2013.01)

(58) Field of Classification Search
CPC ..... A61B 5/0066; A61B 5/0073; A61B 5/682; A61C 9/0073
See application file for complete search history.

(56) References Cited

U.S. PATENT DOCUMENTS

2002/0055082 A1*  5/2002  Durbin ................... A61C 9/00
                                                    433/29

FOREIGN PATENT DOCUMENTS

JP         2008058138 A  *  3/2008

OTHER PUBLICATIONS

Machine translation of Yasunori et al (JP 2008058138 A), accessed on Dec. 2, 2019, pp. 1-9 (Year: 2019).*

* cited by examiner

*Primary Examiner* — Edward Park

(57) ABSTRACT

An intraoral scanning apparatus has a source of low coherence light. An interferometer directs the low coherence light to a reference path and a sample path and generates image data according to interference from combined light returned along the reference and sample paths. A fixture is optically coupled to the sample path and has a bite portion featured for clamping between the jaws of a patient, a track that defines a curved scan path for scanning, one or more scanners configured to direct the sample path light to and from the teeth, and an actuator and translation apparatus that urges the one or more scanners along the curved scan path. A control logic processor synchronizes light scanning and acquisition from the fixture. A display is in signal communication with the control logic processor for display of acquired scan data.

17 Claims, 17 Drawing Sheets

*FIG. 13A*
*FIG. 13B*
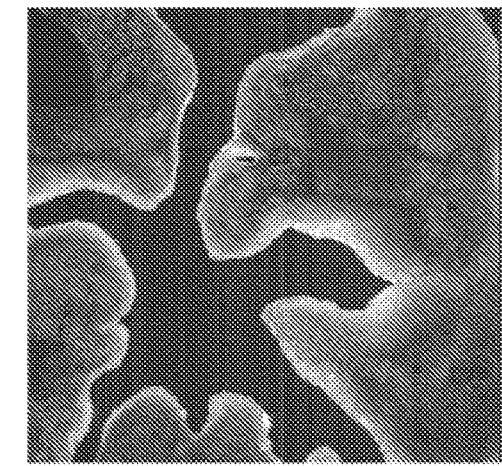
*FIG. 13C*
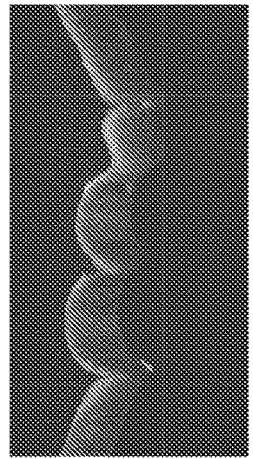
*FIG. 13D*

AUTOMATIC INTRAORAL 3D SCANNER WITH LOW COHERENCE RANGING

TECHNICAL FIELD

The disclosure relates generally to intraoral diagnostic imaging and more particularly to an apparatus and method for intraoral scanning. More specifically, the disclosure relates to scanning apparatus and methods for generating a depth-resolved 3D image of a patient's teeth.

BACKGROUND

Growing interest in the capabilities provided by depth-resolved imaging of the teeth has resulted in the development of various types of hand-held scanners using Optical Coherence Tomography (OCT). Using an OCT scanner, a dental practitioner can obtain depth-resolved image data that shows not only surface structure, but features of the tooth that lie within the tooth structure, aiding diagnosis of disease and providing useful for dental surgery, orthodontia, and dental impressions. In addition, disease conditions such as deep caries can be detected.

Among problems with existing solutions is the need for accurate and stable positioning of the OCT probe. With hand-held OCT devices, it can be very difficult to maintain control of the probe in its course over the tooth surface. Poorly controlled movement of the probe can result in inconsistent or incomplete depth data, requiring considerable processing resources to compensate for positioning inaccuracy and unintentional probe movement during the scan process. It can be very difficult to obtain accurate images of more than one or two teeth at a time. Scanning the whole mouth of the patient to obtain accurate images from each tooth is not feasible when using manual scanner methods. Instead, individual teeth must be scanned separately, with subsequent digital image processing needed in order to piece together enough information to characterize more than a few teeth at a time.

Reference is made to WO 2015/144875 by Berner et al. and to U.S. Pat. No. 8,989,567 to Pulido et al.

Thus, there is a need for methods and apparatus that surmount these problems and provide accurate depth-resolved imaging data over multiple teeth for proper intraoral surface characterization.

SUMMARY

An object of the present disclosure is to address the need for accurate characterization of teeth and other intraoral structures. Embodiments of the present disclosure employ techniques that can automate scanning and subsequent image capture so that full mouth imaging can be obtained without highly sophisticated, stationary imaging systems.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the application, there is provided an intraoral scanning apparatus that can include a) a source of low coherence light, b) an interferometer that directs the low coherence light to a reference path and a sample path and that generates image data according to interference from combined light returned along the reference and sample paths, c) a fixture that is optically coupled to the sample path, wherein the fixture includes (i) a positioning portion configured to extend between the jaws of a patient, (ii) a track that defines a curved scan path for scanning, (iii) one or more scanners configured to direct the sample path light to and from the teeth, (iv) an actuator and translation apparatus that urges the one or more scanners along the curved scan path, d) a control logic processor that synchronizes light scanning and acquisition from the fixture, and e) a display in signal communication with the control logic processor for display of acquired scan data.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 13A shows a 3D surface contour image obtained using an intraoral system of the present disclosure.

FIG. 13B shows a 3D image generated using an intraoral system of the present disclosure.

FIG. 13C shows a typical enface section that can be obtained using an intraoral system of the present disclosure.

FIG. 13D shows an image with depth sectioning of a tooth as obtained by the intraoral imaging apparatus.

DESCRIPTION OF EXEMPLARY EMBODIMENTS

Figure 1:
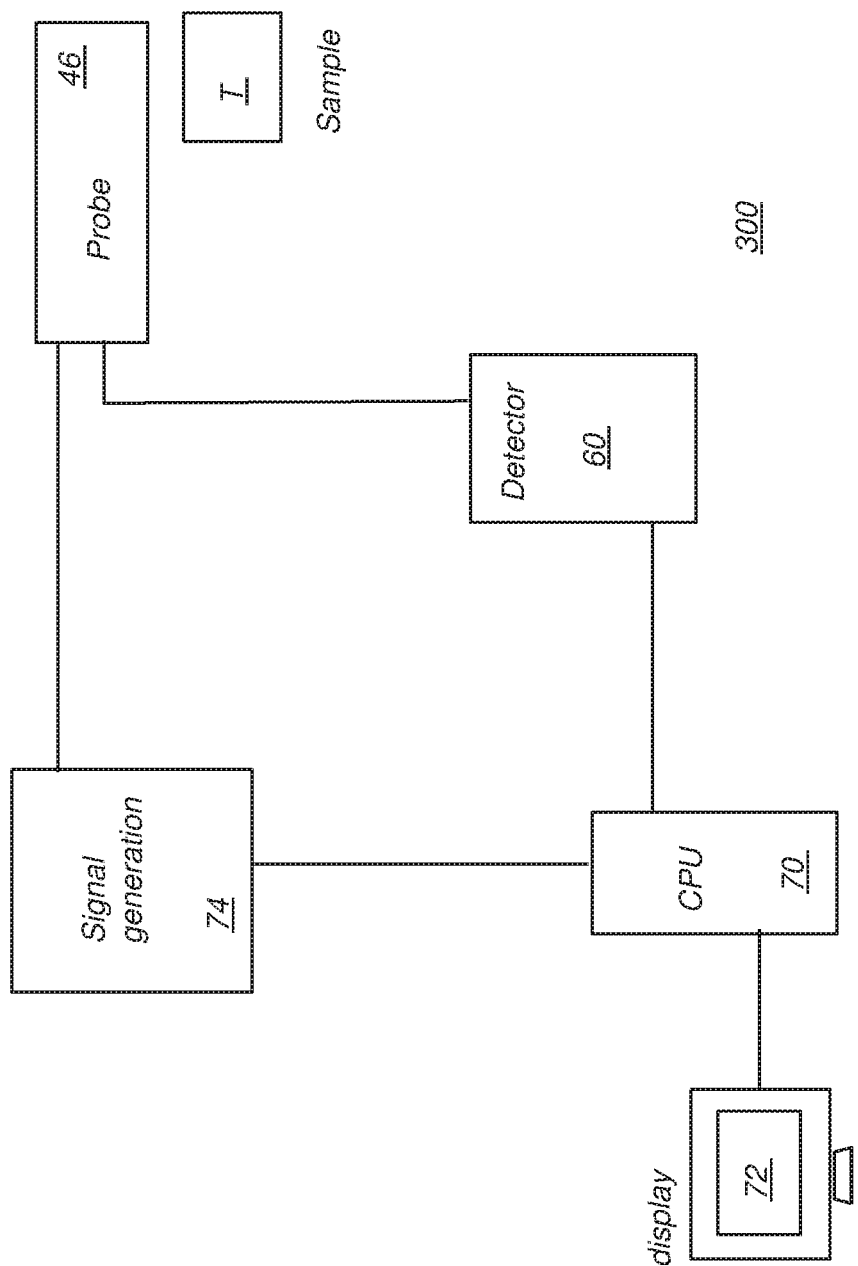
FIG. 1 is a simplified schematic view of a depth-resolved imaging apparatus for intraoral imaging.

The following is a description of exemplary method and/or apparatus embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the terms "viewer", "operator", and "user" are considered to be equivalent and refer to the viewing practitioner, technician, or other person who may operate a camera or scanner and may also view and manipulate an image, such as a dental image, on a display monitor. An "operator instruction" or "viewer instruction" is obtained from explicit commands entered by the viewer, such as by clicking a button on the camera or scanner or by using a computer mouse or by touch screen or keyboard entry. The term "subject" refers to the tooth or other portion of a patient that is being imaged and, in optical terms, can be considered equivalent to the "object" of the corresponding imaging system.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "camera" relates to a device that is enabled to acquire a reflectance, 2D digital image from reflected visible or NIR (near-infrared) light, such as structured light that is reflected from the surface of teeth and supporting structures.

In the context of the present disclosure, the descriptive phrase "mechanically coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components. The phrase "optically coupled" indicates that the corresponding optical components are suitably disposed to pass an optical signal between them.

Certain exemplary method and/or apparatus embodiments of the application can provide a depth-resolved volume imaging for obtaining signals that characterize the surfaces of teeth, gum tissue, and other intraoral features.

Imaging Apparatus

FIG. 1 shows a simplified schematic view of a depth-resolved imaging apparatus 300 for intraoral imaging. Under control of a central processing unit, CPU 70, and signal generation logic 74 and associated support circuitry, a probe 46 directs an excitation signal into the tooth or other intraoral feature, shown as a sample T in FIGS. 1-3 and subsequent figures. Probe 46 can be hand-held or can be gripped or otherwise temporarily fixed in place inside the mouth. Probe 46 obtains a depth-resolved response signal, such as reflection and scattered signal, emanating from the tooth, wherein the response signal encodes depth-resolved structure information for the sampled tissue (e.g., tooth, gingival). The response signal goes to a detector 60, which provides circuitry and supporting logic for extracting and using the encoded information. CPU 70 then performs reconstruction of a 3D or volume image of the tooth surface or surface of a related feature according to the depth-resolved response signal. CPU 70 can also perform other types of processing, such as segmentation processing for identifying parts of the sampled tissue for improved 3D surface computation. A display 72 then allows rendering of the 3D surface image content, such as showing individual slices of the reconstructed volume image. Storage and transmittal of the computed surface data or of an image showing all or only a portion of the surface data can also be performed as needed.

Figure 2:
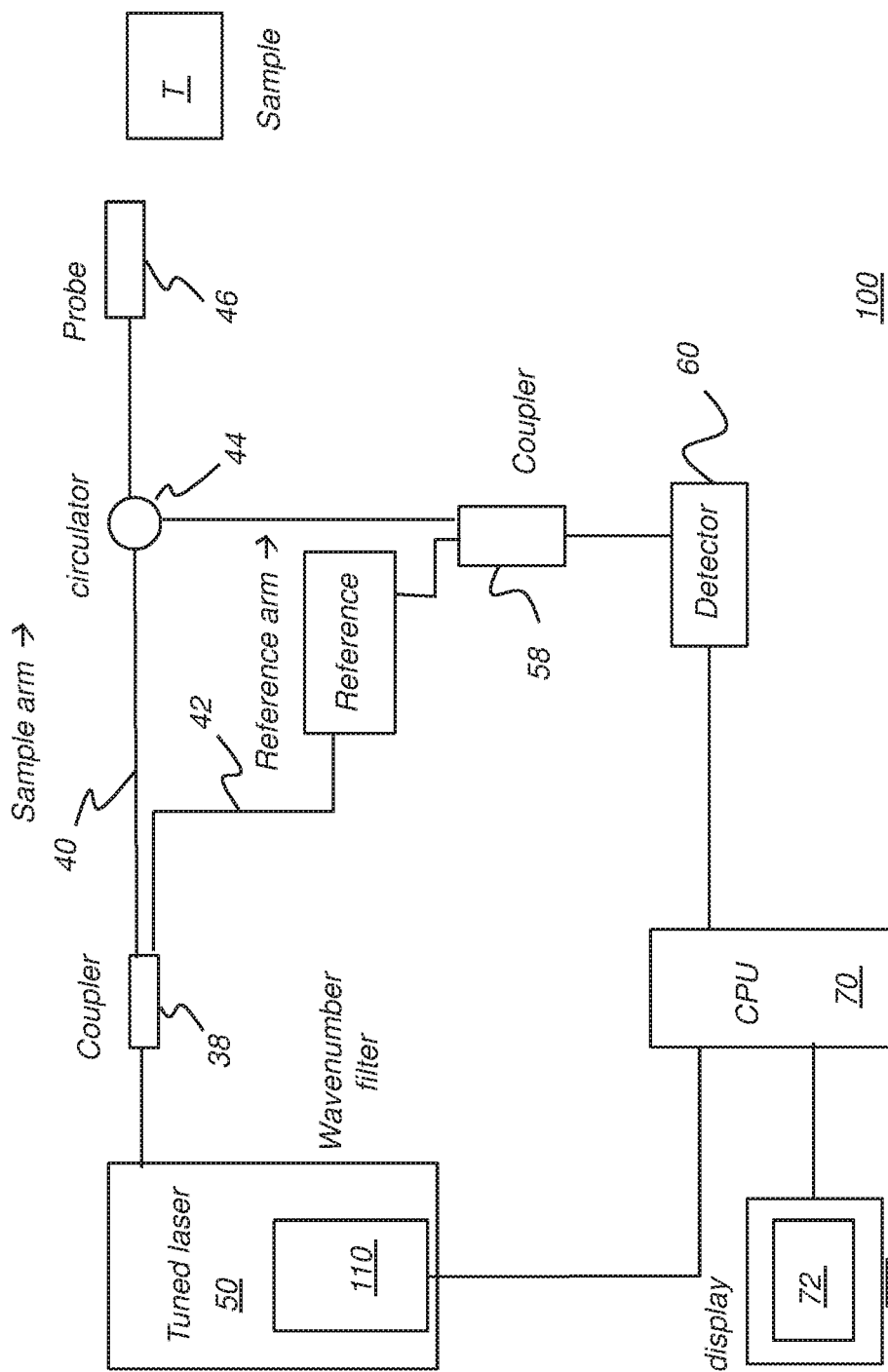
FIG. 2 shows a swept-source OCT (SS-OCT) apparatus using a Mach-Zehnder interferometer system according to an embodiment of the present disclosure.
Figure 3:
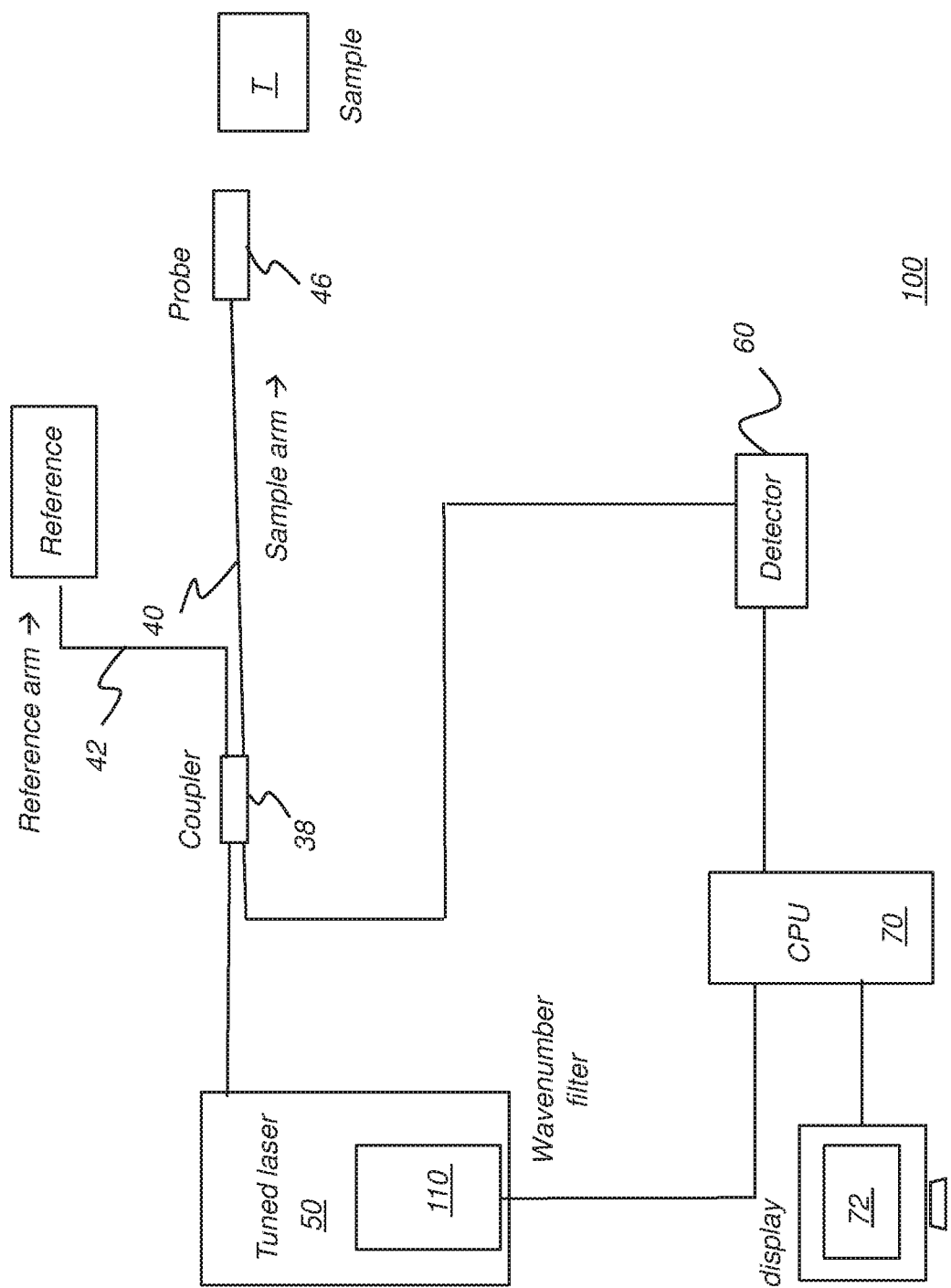
FIG. 3 shows a swept-source OCT (SS-OCT) apparatus using a Michelson interferometer system according to an embodiment of the present disclosure.

The simplified schematic diagrams of FIGS. 2 and 3 each show a swept-source OCT (SS-OCT) apparatus 100 using a programmable filter 110 according to an embodiment of the present disclosure. In each case, programmable filter 110 is used as part of a tuned laser 50 that provides an illumination source. For intraoral OCT, for example, laser 50 can be tunable over a range of frequencies (wave-numbers k) corresponding to wavelengths between about 400 and 1600 nm. According to an embodiment of the present disclosure, a tunable range of 35 nm bandwidth centered about 830 nm can be used for intraoral OCT.

In the FIG. 2 embodiment, a Mach-Zehnder interferometer system for OCT scanning is shown. FIG. 3 shows components for an alternate Michelson interferometer system. For these embodiments, programmable filter 110 provides part of the laser cavity to generate a tuned laser 50 output. The variable laser 50 output goes through a coupler 38 and to a sample arm 40 and a reference arm 42. In FIG. 2, the sample arm 40 signal (e.g., signal T) goes through a circulator 44 and to probe 46 for measurement of a sample tissue (e.g., teeth, dentition). The sampled depth-resolved signal is directed back through circulator 44 (FIG. 2) and to a detector 60 through a coupler 58. In FIG. 3, the signal T goes directly to sample arm 40 and reference arm 42; the sampled signal is directed back through coupler 38 and to detector 60. The detector 60 may use a pair of balanced photodetectors configured to cancel common mode noise. Control logic processor (control processing unit CPU) 70 is in signal communication with tuned laser 50 and its programmable filter 110 and with detector 60 and obtains and processes the output from detector 60. As shown also in FIG. 1, CPU 70 is in signal communication with display 72 for command entry and for OCT results display, such as rendering of the 3D image content from various angles and sections or slices. However, conventional additional operator/command entry devices can be used with exemplary depth-resolved imaging apparatus 300 or exemplary apparatus 100.

Figure 4:
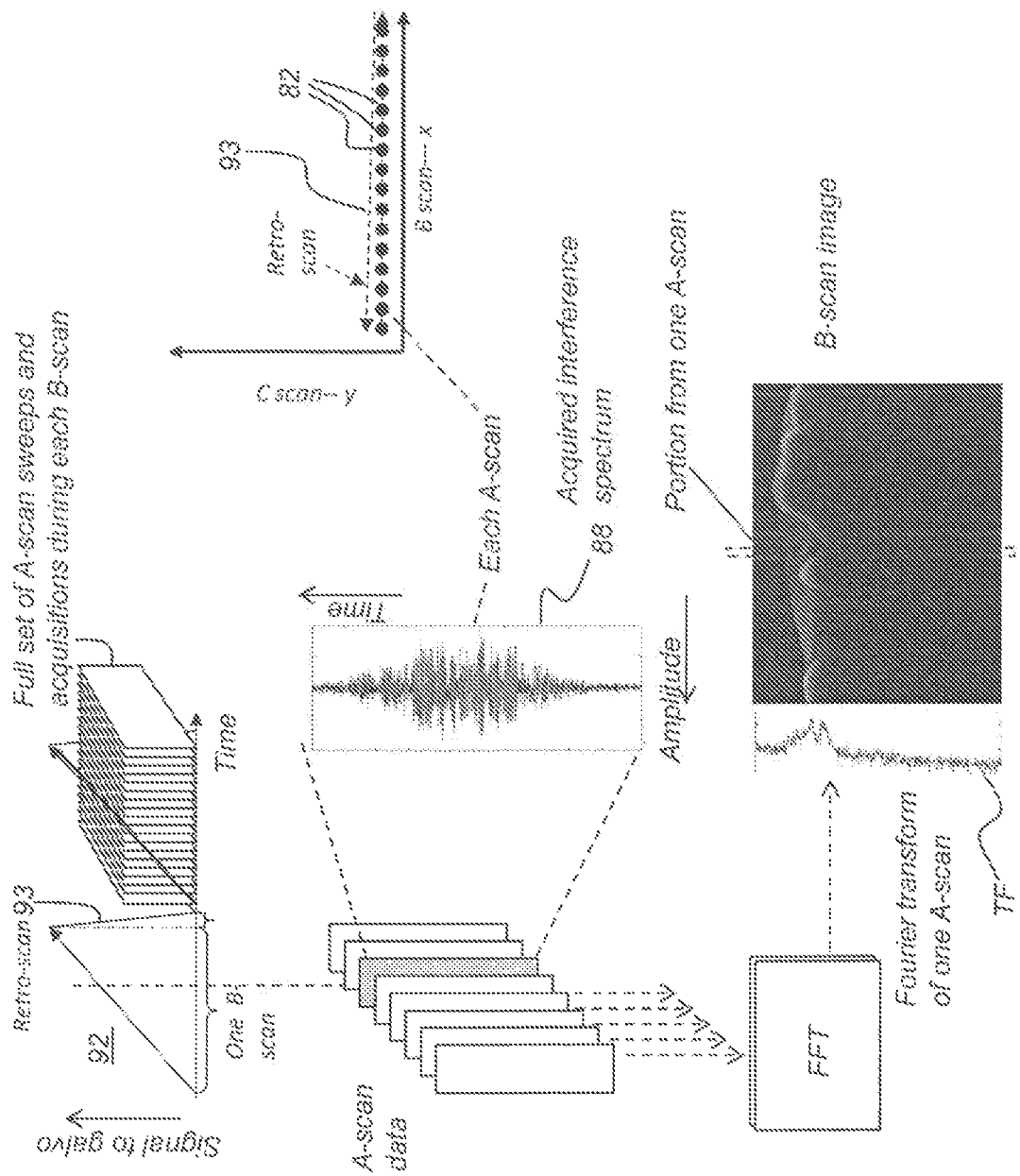
FIG. 4 is a schematic diagram that shows how A-scan, B-scan, and C-scan are related in forming tomographic images of an intraoral feature using the OCT apparatus of the present disclosure.

The schematic diagram of FIG. 4 shows a scan sequence that can be used for forming tomographic images of an intraoral feature using the OCT apparatus of the present disclosure. The sequence shown in FIG. 4 summarizes how a single B-scan image is generated. A raster scanner scans the selected light sequence as illumination over the sample tooth, point by point. A periodic drive signal 92 as shown in FIG. 4 is used to drive the raster scanner mirrors to control a lateral scan or B-scan that extends across each row of the sample, shown as discrete points 82 extending in the horizontal direction. At each of a plurality of points 82 along a line or row of the B-scan, an A-scan or depth scan, acquiring data in the z-axis direction, is generated using successive portions of the selected wavelength band. FIG. 4 shows drive signal 92 for generating a straightforward ascending sequence using the raster scanner, with corresponding tuning of the laser through the wavelength band. The retro-scan signal 93, part of drive signal 92, simply restores the scan mirror back to its starting position for the next line; no data is obtained during retro-scan signal 93.

It should be noted that the B-scan drive signal 92 drives the actuable scanning mechanics, such as a galvo or a microelectro-mechanical mirror, for the raster scanner of the OCT probe 46 (FIG. 2,3). At each incremental scanner position, each point 82 along the row of the B-scan, an A-scan is obtained as a type of 1D data, providing depth-resolved data along a single line that extends into the tooth. To acquire the A-scan data with spectral OCT, a tuned laser or other programmable light source sweeps through the spectral sequence. Thus, in an embodiment in which a programmable filter causes the light source to sweep through a 30 nm range of wavelengths, this sequence for generating illumination is carried out at each point 82 along the B-scan path. As FIG. 4 shows, the set of A-scan acquisitions executes at each point 82, that is, at each position of the scanning mirror. By way of example, there can be 2048 measurements for generating the A-scan at each position 82.

FIG. 4 schematically shows the information acquired during each A-scan. An interference signal 88, shown with DC signal content removed, is acquired over the time interval for each point 82, wherein the signal is a function of the time interval required for the sweep (which has a one-to-one correspondence to the wavelength of the swept source), with the signal that is acquired indicative of the spectral interference fringes generated by combining the light from reference and feedback (or sample) arms of the interferometer (FIGS. 2, 3). The Fourier transform generates a transform TF for each A-scan. One transform signal corresponding to an A-scan is shown by way of example in FIG. 4.

From the above description, it can be appreciated that a significant amount of data is acquired over a single B-scan sequence. In order to process this data efficiently, a Fast-Fourier Transform (FFT) is used, transforming the spectral-based signal data to corresponding spatial-based data from which image content can more readily be generated.

In Fourier domain OCT, the A scan corresponds to one line of spectrum acquisition which generates a (z-axis) line of depth resolved OCT signal. The B scan data generates a 2D OCT image as a row R along the corresponding scanned line. Raster scanning is used to obtain multiple B-scan data by incrementing the raster scanner acquisition in the C-scan direction.

An embodiment of the present disclosure uses a low-coherence light source, such as an SLD (super-luminescent diode) for example, with an intraoral fixture and scan pattern that is suited for controlled, successive scanning of multiple teeth. The scan pattern is particularly adapted to facilitate automated image capture and processing for accurately characterizing tooth structure with depth-resolved OCT imaging.

Figure 5:
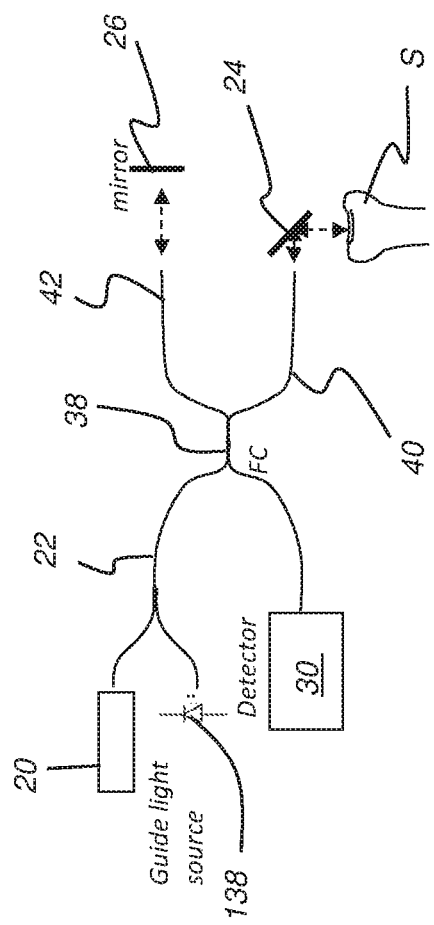
FIG. 5 is a schematic diagram that shows use of a broadband light source with components for intraoral OCT imaging, with the light source coupled into a single mode optical fiber from one distal end.

The schematic diagram of FIG. 5 shows use of a broadband light source 20 coupled into a 2×2 single mode optical fiber 22 from one distal end for intraoral OCT imaging, according to an embodiment of the present disclosure. The broadband light is split into reference light and sample light (e.g., to sample T), following the basic pattern outlined with reference to FIGS. 2 and 3. Sample light output from the sample arm 40 is collimated then steered by a scan mirror 24 such as MEMS scanner, galvo scanner, or other scanner apparatus. This scanned light is focused onto and scattered by tissue on and beneath the surface of the sample S. Backscattered light from the sample S is coupled into the sample arm fiber via the common optical scan path. Reference light is retro-reflected from a reference mirror 26. Reference light from reference arm 42 interferes with the backscattered sample light at the 2×2 fiber coupler 38. Interference light is delivered into a customized spectrometer, shown as a detector 30. One line of spectrum is acquired, processed, transformed into a line of depth resolved signal corresponding to each scan point at the sample S.

The scan mirror 24 directs a 1D raster scan to the sample S at a relatively slow speed, for instance, 25 fps (frames per second). For intraoral imaging, the scan width can be between 10-15 mm for each scan line. A 1D interference spectrum is synchronously acquired for each scan point of the 1D scan line. For example, 1000 lines of spectrum are acquired, at a nominal 25 k line/s acquisition speed for maintaining 25 fps. This gives a scanned digital resolution in the 10-15 μm range. The lateral optical resolution is determined by the focused scan waist. The depth resolution is inversely proportional to the bandwidth of light source 20. Thus, the wider the light beam from light source 20, the higher the depth resolution. By way of example, the depth resolution can be 5.6 μm, with center wavelength 800 nm and 50 nm bandwidth light source 20.

Continuing with the description of FIG. 5, a guide light source 138 can be provided for helping to provide illumination within the mouth of the patient in order to improve positioning of scanning components.

Figure 6:
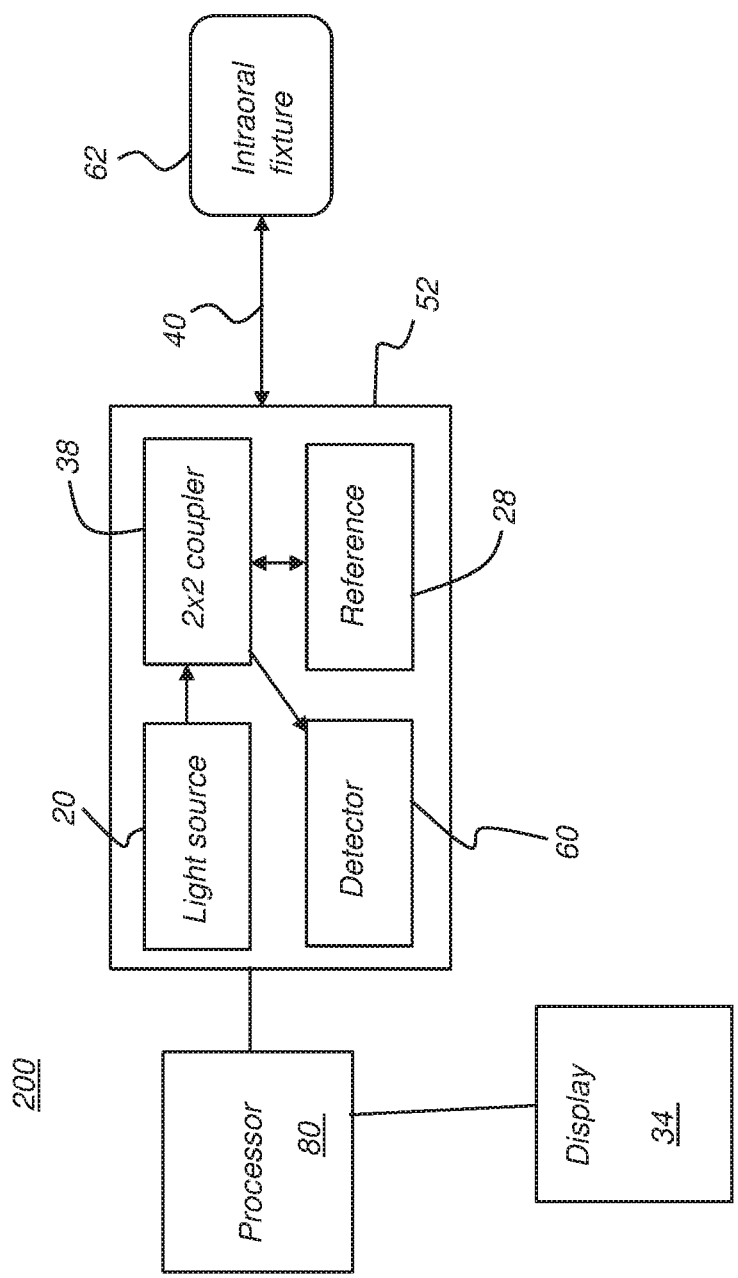
FIG. 6 is a schematic diagram that shows components of a depth-resolved intraoral imaging apparatus.

FIG. 6 is a schematic diagram that shows components of a depth-resolved imaging apparatus 200. In an imaging engine 52, light source 20 directs light through a 2×2 fiber coupler 38 which directs light to a reference 28 and to sample arm 40 that is optically coupled to an intraoral fixture 62. Modulated light from fixture 62 is then routed back by coupler 38 to detector 60, an interferometric apparatus. A processor 80, such as a computer or dedicated control logic processor, for example, then provides the control and operational logic for functions of apparatus 200. A display 34 is in signal communication with processor 80 for display of imaging results.

Figure 7:
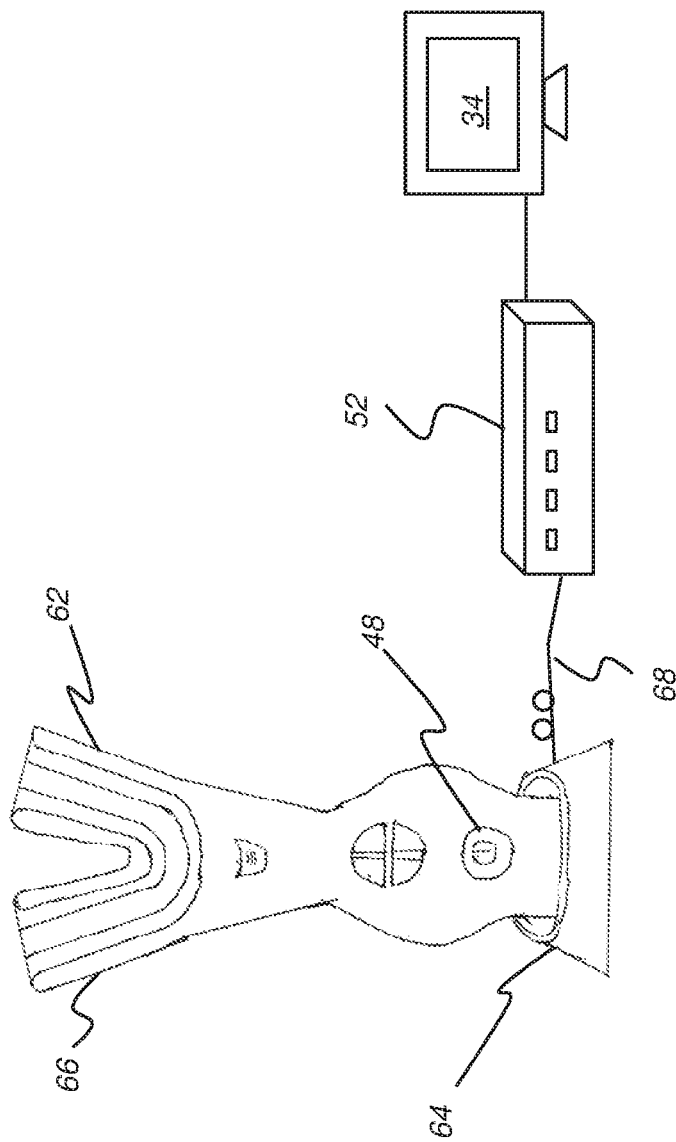
FIG. 7 is a schematic view that shows components of a depth-resolved imaging apparatus.

The schematic view of FIG. 7 shows components of depth resolved imaging apparatus 200 with intraoral fixture 62 having a holder 64 that can be used for seating the device when not in use. The holder 64 can provide power and/or protection when the intraoral fixture 62 is not in use. A control such as an operator control switch 48 can be provided for initiation or pausing of the scan sequence, as described in more detail subsequently. In the exemplary embodiment shown in FIG. 7, imaging engine 52 includes an integrated processor (not shown) for control of imaging apparatus 200 functions. Imaging engine 52 can include any or all of the components shown in FIG. 6, for example. Imaging engine 52 is connected to intraoral fixture 62 through a cable 68, which can include wiring for electrical signals and power and the sample arm optical fiber 40.

Figure 8:
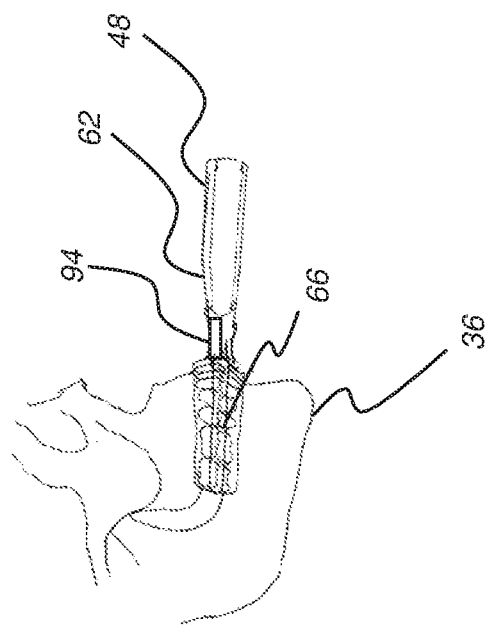
FIG. 8 is a side view that shows an intraoral fixture as it is positioned to scan the mouth of a patient, according to an embodiment of the present disclosure.

FIG. 8 is a side view that shows intraoral fixture 62 as it is positioned for scanning teeth within the mouth of a patient 36, according to an embodiment of the present disclosure. Patient 36 holds fixture 62 by biting down on the device, gripping fixture 62 in place, clamped within the jaws during the scan. Control switch 48 allows the patient to initiate the scan sequence for self-scanning, without the assistance of a technician or practitioner. An optional camera 94 is mounted within fixture 62 for providing a preview image that shows at least some portion of the scan area. According to an embodiment of the present disclosure, preview camera 94 displays a reflective image that is indicative of fixture 62 position on display 34 (FIG. 6). The image can be in two or more colors (polychromatic) or monochrome, for example. This display allows the viewer or other technician or practitioner to determine whether or not further adjustment or re-positioning of the fixture 62 would be useful for subsequent OCT scanning. This feature can be of particular utility where it is useful to place fixture 62 for scanning a partial subset of the dental arch, such as where one or more teeth are to be scanned.

According to an embodiment of the present disclosure, the fixture 62 has a scanning orientation, so that the scanning apparatus can be positioned to face either the upper or the lower dental arch. This configuration enables fixture 62 to be reversed for separately scanning each half of the patient's dentition.

Fixture 62 can alternately have an inner track that has an external motor for urging the scanner 130 along a suitable track for the patient. Adjustment for different arch dimensions can also be provided.

Figure 9B:
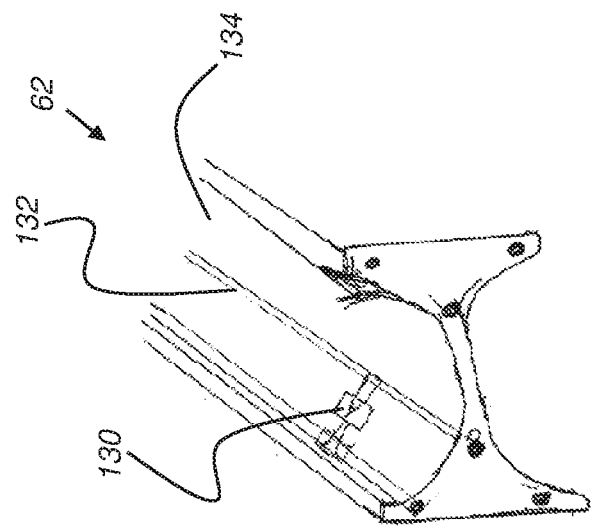
FIGS. 9A and 9B show a cross-sectional and cross-sectional perspective view, respectively, of scan components within an intraoral fixture.
Figure 9A:
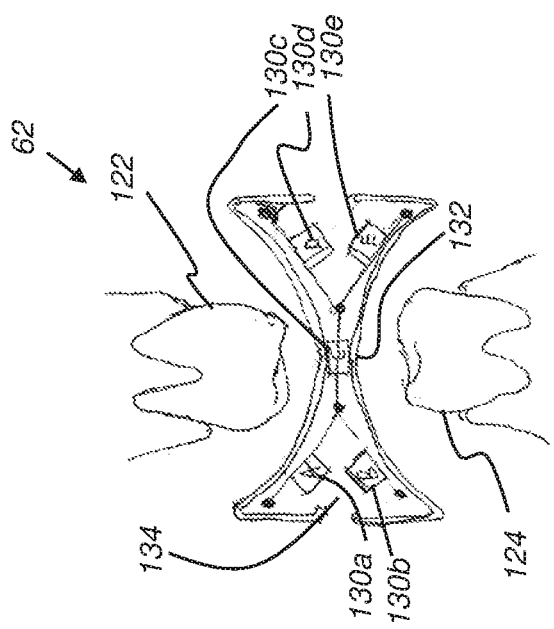

FIGS. 9A and 9B show cross-sectional and cross-sectional perspective views, respectively, of scanner components for various embodiments of intraoral fixture 62. One or more scanners 130 are each guided along a track 132 within fixture 62 in order to perform the B-scan irradiation of the OCT light pattern against tooth 122, 124 and related intraoral features. Track 132 can have any suitable arrangement for guiding the scanner(s) along the curved path.

By way of example, a bank or set of five scanners is provided in the embodiment shown in FIG. 9A. Scanners can be exposed or behind a transparent cover. The complete set of scanners 130 is urged along a track 132 within a channel 134, scanning orthogonally with respect to the curved track 132 in order to provide x-scan (C-scan) movement. Scanners 130a and 130b scan the lingual surfaces of the teeth; scanners 130d and 130e scan the buccal surface. One or more scanners 130c scan central portions of the chewing surfaces of the teeth. Generally, scanned regions of adjacent surfaces have some overlaps. If scanners 130a, 130b, 130d, and 130e have large enough field-of-view, it can be possible for their combined scanned regions to completely cover the occlusal surfaces, without requiring an additional scanner 130c. Separate scanners can be provided for scanning maxillary and mandibular tooth structures, using the same track 132 or using multiple tracks. With the banked arrangement of FIG. 9A, for example, both maxillary and mandibular arches can be scanned in a single pass. Scanners 130 are each optically coupled to the sample arm 40 (FIGS. 5, 6) through an optical fiber that is capable of bending to follow scan path curvature as scanning progresses along track 132. Mechanical coupling to an actuator provides the needed motion along track 132. Individual signals from the multiple scanners 130 can be detected by detector 60 in a time-multiplexed manner.

FIG. 9B shows a single scanner 130, capable of scanning along one section of track 132 at a time. Multiple passes of scanner 130 can be used for depth-resolved characterization of different teeth surfaces.

Figure 9C:
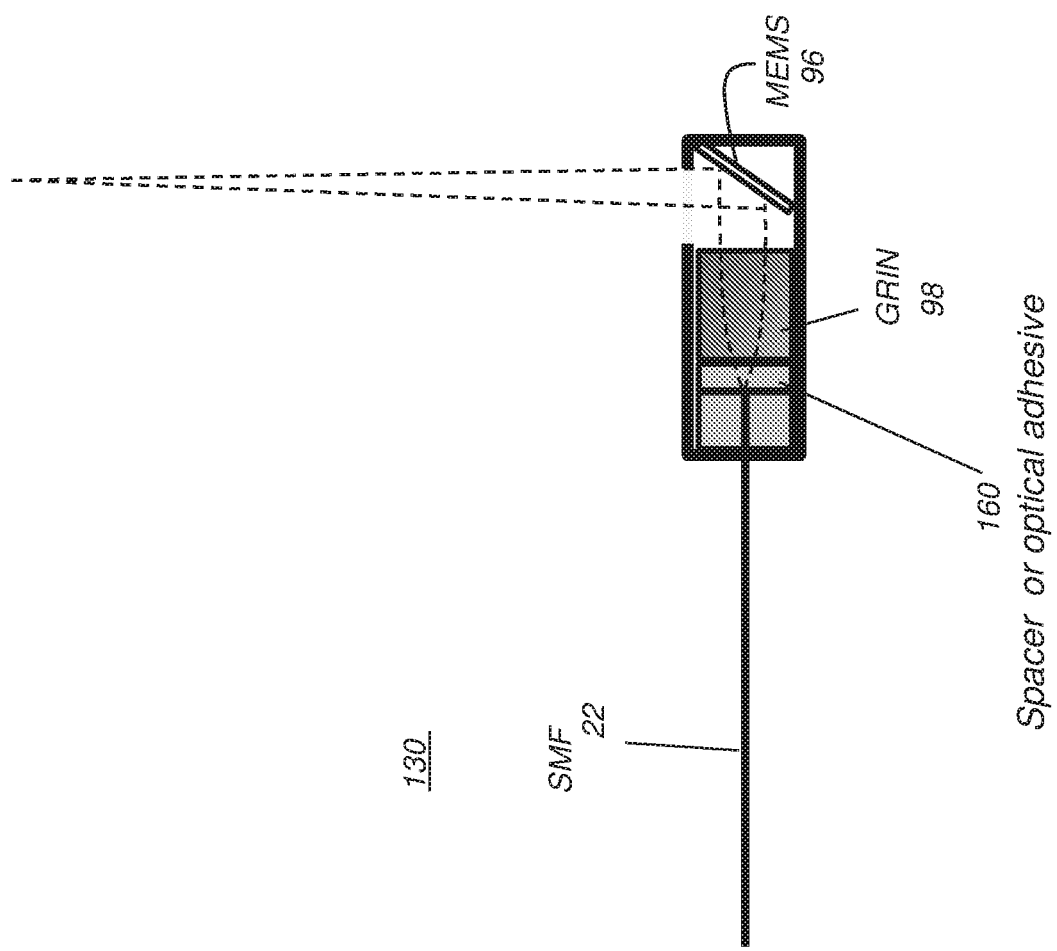
FIG. 9C is a schematic side view showing components of a scanner for the intraoral fixture according to an embodiment of the present disclosure.

Various types of scanner 130 design can be used. FIG. 9C is a schematic side view showing components of a scanner 130 for the intraoral fixture according to an embodiment of the present disclosure. Here, scanner 130 uses a microelectromechanical systems (MEMS) device 96 that provides a rapidly movable reflective surface for deflecting the scanning light energy from single-mode fiber 22 to provide the B-scan, with illumination in one direction, out toward the tooth or other subject anatomy and feedback, in the opposite direction, back to the interferometer or other detector for analysis. A tiny gradient index or GRIN lens 98 or other type of optic is used for conditioning the light path for scanner energy. Optical coupling of the light to and from fiber 22 to lens 98 can be through a spacer 160 or using optical adhesives, for example.

Figure 9D:
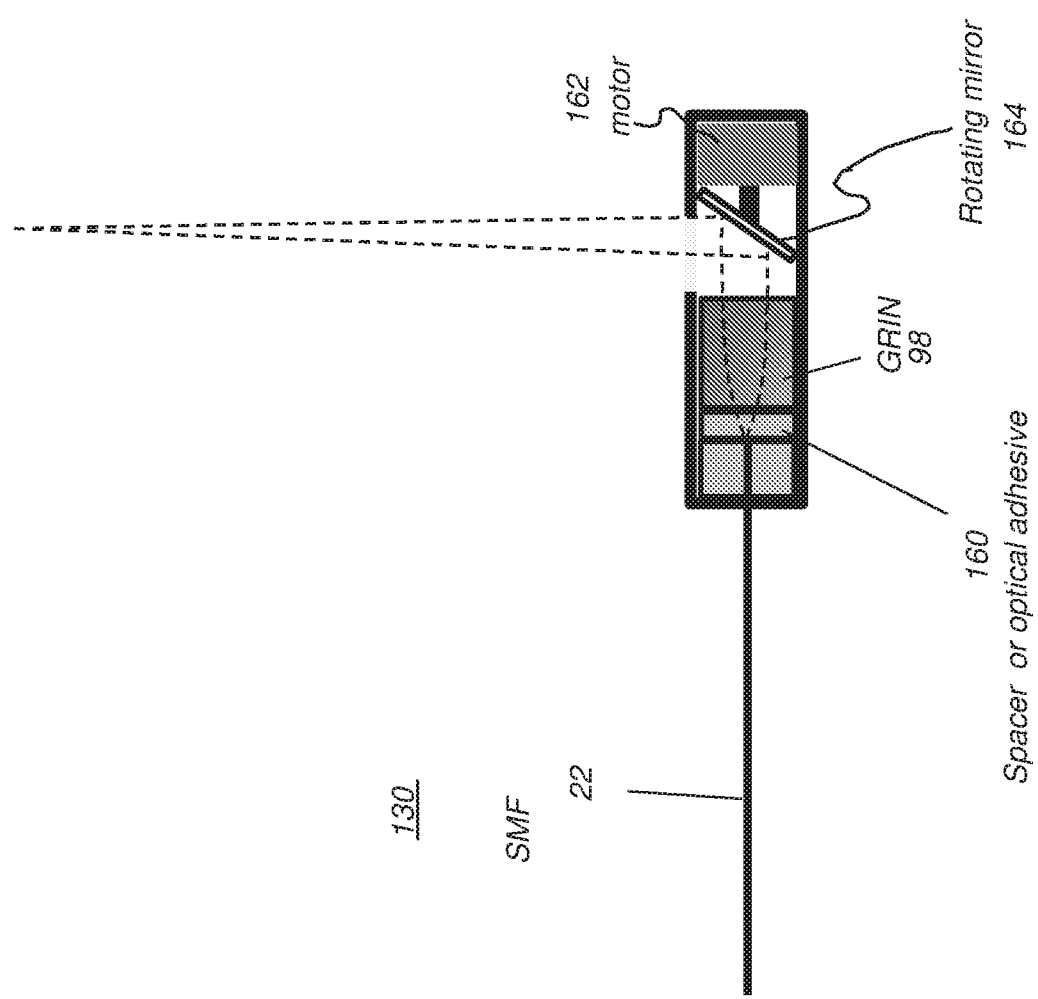
FIG. 9D is a schematic side view showing components of a scanner for the intraoral fixture according to an alternate embodiment of the present disclosure.

FIG. 9D is a schematic side view showing components of a scanner 130 for the intraoral fixture according to an alternate embodiment of the present disclosure. GRIN lens 98 and coupling components are similar to those of FIG. 9C. Scanner illumination is provided by deflection using a motor 162 that drives a reflective surface 164 to effect the B-scan.

Figure 10A:
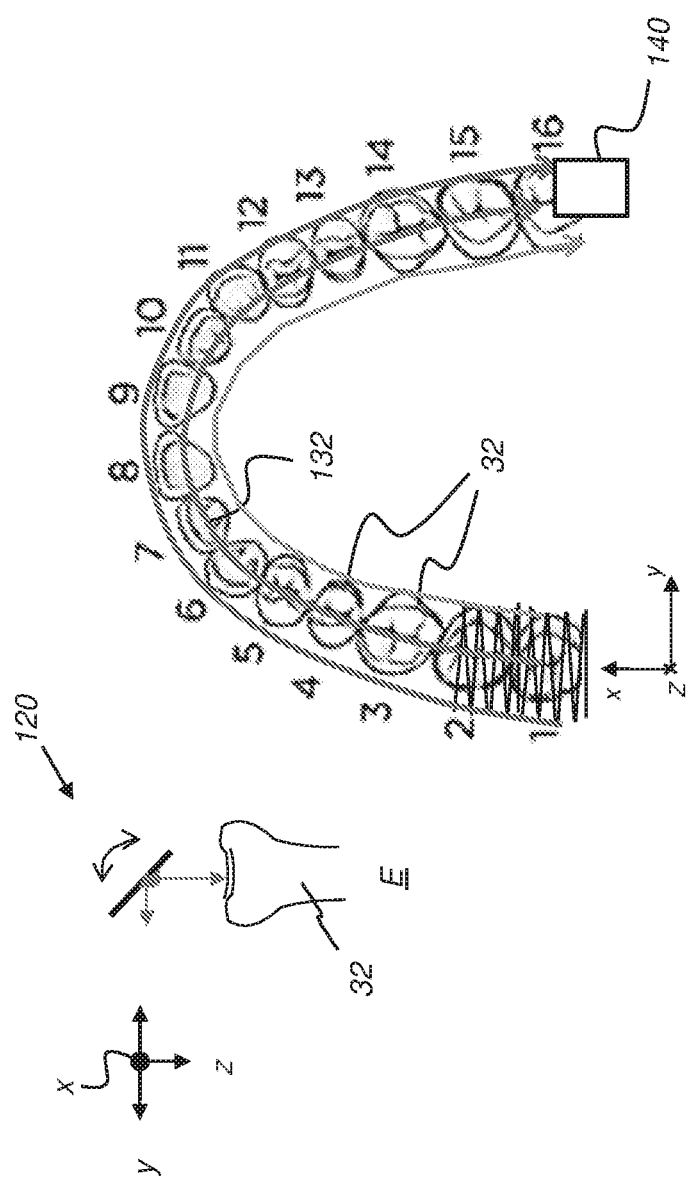
FIG. 10A is a schematic diagram that shows, from a top view, details of the raster scan, with 3D orthogonal coordinate mapping for reference.
Figure 10B:
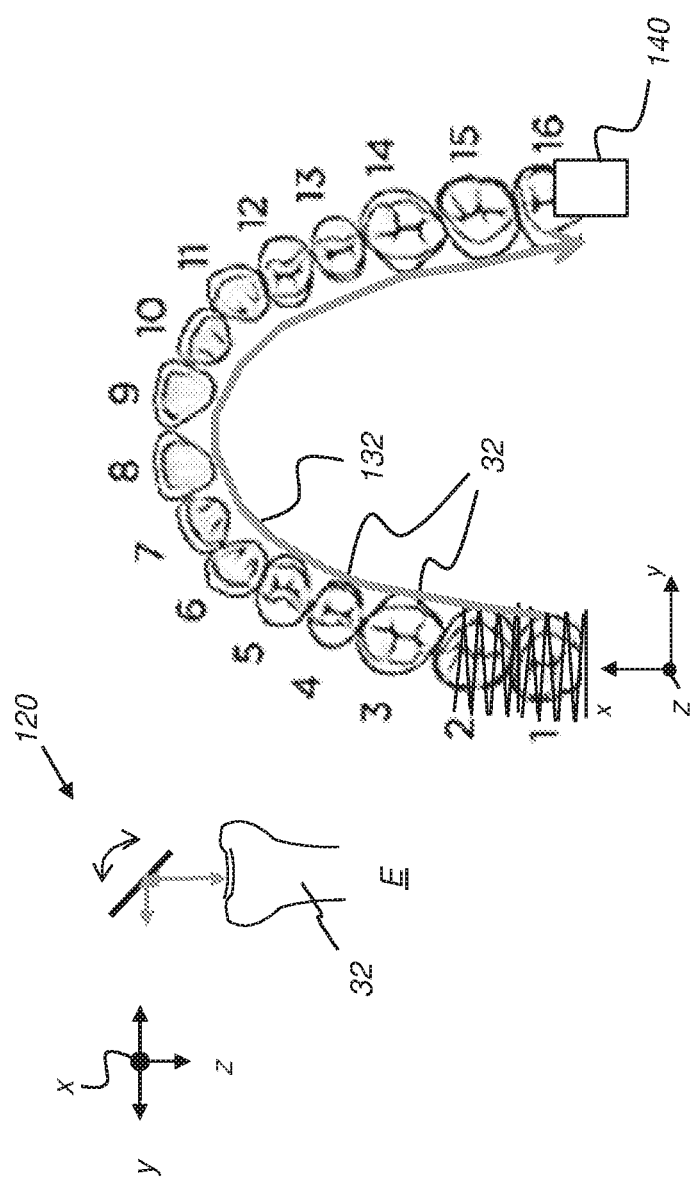
FIG. 10B is a schematic diagram that shows a top view of one portion of the raster scan.
Figure 10C:
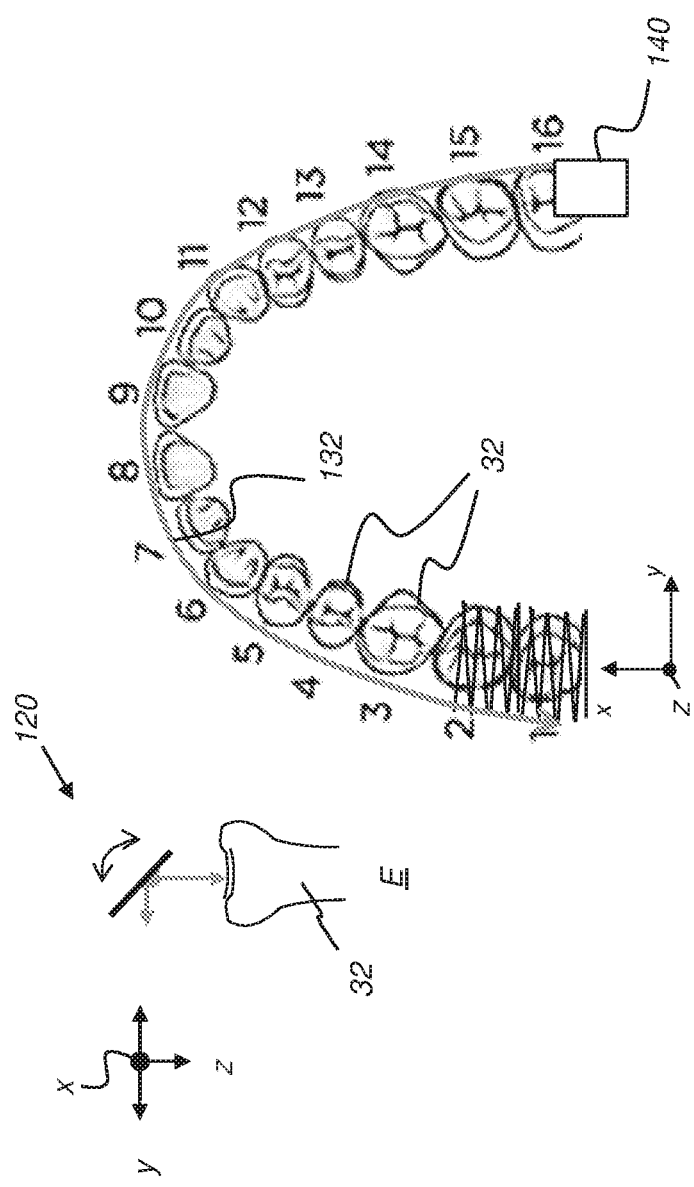
FIG. 10C is a schematic diagram that shows a top view of the other portion of the raster scan that complements the scan provided in FIG. 10B.

Referring to FIGS. 10A, 10B, and 10C, each arrangement of scanners 130 follows track 132 to provide one or more scan paths. Track 132 is curved to follow the curved arrangement of teeth 32 within the jaw. The fixture 62 arrangement shown in FIG. 9A provides multiple scanners, allowing a single-pass scanning arrangement as shown in FIG. 10A, that can provide depth-resolved imaging for both maxillary and mandibular arches.

The FIGS. 10B and 10C scan paths can be used where a single scanner 130 is provided within fixture 62, as shown in FIG. 9B. The scanner can be oriented such that its field-of-view covers both smooth and biting surfaces. In a first pass, buccal and occlusal surfaces can be scanned. Then, with scanner 130 flipped in orientation (manually or using a stepper motor, for example) and then urged along path 132 in the opposite direction, lingual and occlusal surfaces can be scanned.

According to an alternate embodiment of the present disclosure, fixture 62 is configured to scan only the maxillary or only the mandibular arch at a time. With reference to FIG. 8, the patient scans the upper arch, with fixture 62 in a first orientation performing the appropriate scan shown in FIGS. 10A-10C. The patient then reverses the orientation of fixture 62 to scan the mandibular arch in a subsequent scan.

Using the scan arrangement of FIGS. 10A-10C, each B scan yields a 2D depth section in the y-z plane, using the coordinate designations shown. The B scan orientation is relative to axis y, with a scan path and, for the sequence using FIGS. 10B and 10C, a return path. Axis z, into the page in the top view of FIGS. 10A-10C, and downwards in the enlarged side view E at the left, is the depth orientation. The third dimension x scan is implemented by urging a scanner apparatus 120 along the curved path of track 132. An actuator 140 urges the scanning apparatus 120 forward along the curved path. Teeth are numbered 1-16 to correspond to conventional dental tooth numbering for the lower mouth. A full 3D image of the teeth can be formed by stitching the 2D images together as acquired along the curved path, in the x direction as shown.

Any of a number of types of conventional drives such as motors, electromechanical mechanisms or other devices can be used as actuator 140 that is mechanically coupled to scanners 130 for providing prescribed translation (e.g., linear or non-linear) along track 132. According to an embodiment of the present disclosure, actuator 140 can be a motor that urges scanner(s) 130 along track 132 using a cord or string. A pulley mechanism can be provided for providing this C-scan or x-axis motion of scanner(s) 130 along curved track 132.

The exemplary embodiments of FIGS. 7-10C provide a fixture 62 that, once fitted into position and held in place, such as by the patient's bite, can be used to scan multiple teeth, the complete upper or lower dental arch, or even, given the appropriate fixture 62 design of FIG. 10A, all of the upper teeth or all of the lower teeth of the patient at a time. As noted previously, to scan the full mouth, the patient can insert bite portion 66 to scan the lower teeth first, then reverse the vertical orientation of fixture 62 in order to scan the upper teeth. Alternately, the upper arch can be scanned first, followed by the lower arch. In addition, the device can be controlled, using commands from a processor or computer, to scan only a portion or selected portions of the full dental arch as required by the practitioner.

According to an embodiment of the present disclosure, for the set of teeth including facial, occlusal, and lingual scans, each scan takes about 93 s with x,y scan resolution of 30 μm, 500 lines/B scan at an acquisition speed of 25 k line/s, calculated using an average adult tooth length of about 14 cm. The y scan length is in the 10-15 mm range. The complete lower arch scan using these values takes approximately 180 seconds=3 minutes, if three passes are used.

It should be noted that different sizes of fixture 62 can be used for patients of different mouth sizes, allowing a suitable scan arrangement for patients having different builds. Alternately, an adjustable fixture can be provided, using a hinged arrangement, for example to suit the fixture to the arch shape of a particular patient. Control software can be programmed to restrict the scan to a limited portion of the non-linear, curved or arcuate scan path. Additional features of exemplary fixture 62 can be used to easily position the fixture 62 relative to a patient's teeth or arch. In some exemplary embodiments, fixture 62 can be removably fixed to the patient's upper or lower jaw or positioned at the patient's upper or lower jaw for depth resolved image scanning so that the patient need not bite down on the fixture 62 during a scan. In one exemplary embodiment, the fixture 62 can be held in place by tension or elasticity characteristics that push against multiple (e.g., opposing) sides of the inside or the outside of the upper or lower jaw. In one exemplary embodiment, the fixture 62 can be held in place by portions of the teeth, jaw or dentition not being scanned.

Scanning Sequence

Figure 11:
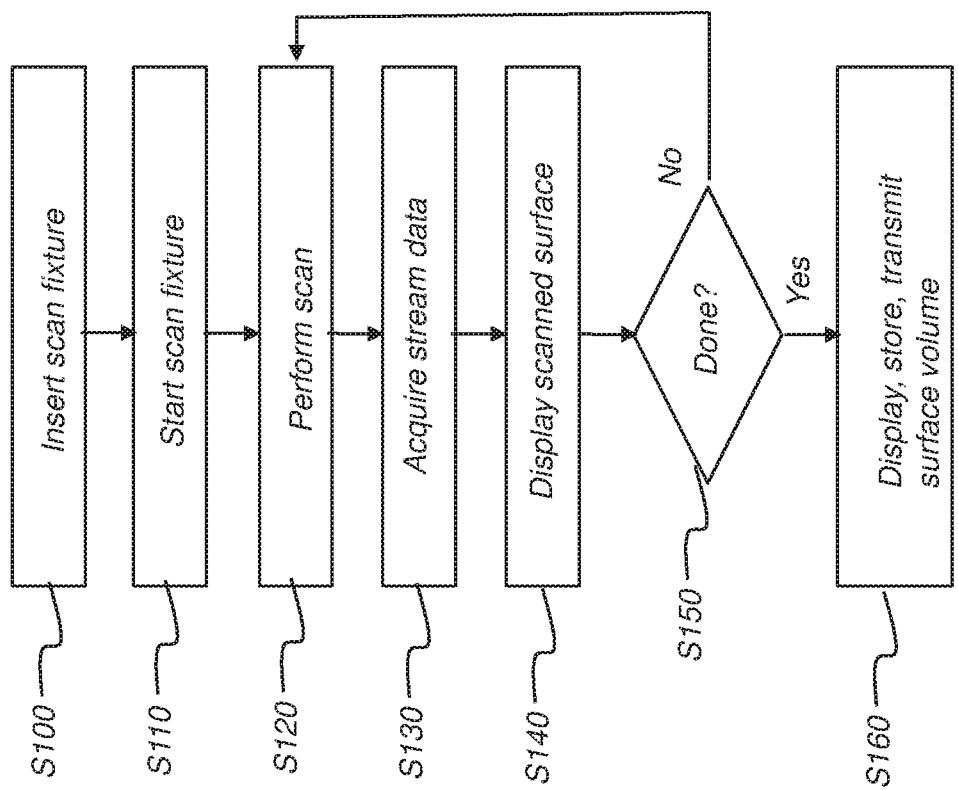
FIG. 11 is a logic flow diagram that shows a scanning sequence according to an embodiment of the present disclosure.

FIG. 11 is a logic flow diagram that shows a scanning sequence according to an embodiment of the present disclosure. In a setup step S100, the patient, technician, or practitioner inserts intraoral scanning fixture 62 into the mouth of the patient. The patient can bite down to hold fixture 62 in place. In an initiation step S110, the patient or technician/practitioner powers up the fixture 62 for scanning. Fixture 62 scanner components can be reset to a start position for the scan. In a scanning step S120, the scan is executed, with scanner travel, B-scan pattern scanning causing the scanner mirrors to move along track 132, as shown earlier with reference to FIG. 10. In a data acquisition step S130 spectral image data from the intraoral fixture 62 is acquired and transmitted to processor 60 (FIG. 6). A display step S140 then displays scanned surface data from the recently acquired depth-resolved tooth images as it is obtained and pre-processed. In a decision step S150, system logic determines whether or not the full scan by the fixture is completed. Until the scan is complete, steps S120, S130, and S140 are continuously executed, acquiring and updating scanned image data. A volume display, store, transmit step S160 then forms a 3D surface volume for display, storage, or transmission.

Image Processing

Figure 12B:
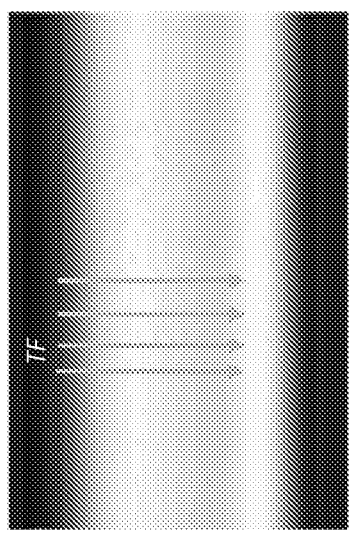
FIG. 12B shows a reconstructed image formed from depth-resolved scan data.
Figure 12A:
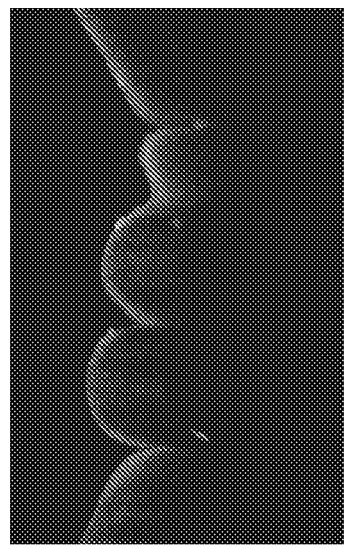
FIG. 12A shows a small set of successive A-scans for obtaining the depth-resolved signals processed by a Fourier transform and used for forming the OCT image.

FIG. 12A shows a small set of successive A-scans for obtaining the depth-resolved signals processed by a Fourier transform (TF) and used for forming the OCT image. The data FIG. 12B shows a reconstructed image formed from the depth-resolved scan data.

FIG. 13A shows a 3D surface contour image 210 obtained in accordance with certain exemplary method and/or apparatus embodiments of the application. FIG. 13B shows a 3D image 214 reconstructed from scan data. FIG. 13C shows a typical en-face section 212 that can be generated from scan data. FIG. 13D shows a B-scan image 216 with depth sectioning of a tooth as obtained by the intraoral imaging apparatus.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as CPU 70 as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments of the application can provide a depth-resolved volume imaging to characterize surfaces of teeth, gum tissue, and other intraoral features. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. An intraoral scanning apparatus comprising:
   a) a source of low coherence light;
   b) an interferometer that directs the low coherence light to a reference path and a sample path and that generates image data according to interference from combined light returned along the reference and sample paths;
   c) a fixture that is optically coupled to the sample path, where the fixture comprises:
      (i) a positioning portion configured to extend between the jaws of a patient;
      (ii) a track that defines a curved scan path for scanning;
      (iii) one or more scanners configured to direct the sample path light to and from teeth of the patient, wherein each scanner is operable to scan multiple surfaces of teeth at locations along the curved scan path absent lateral movement of the scanner relative to the track;
      (iv) an actuator and translation apparatus that urge the one or more scanners along the curved scan path;
   d) a control logic processor that synchronizes light scanning and acquisition from the fixture; and
   e) a display in signal communication with the control logic processor to display of acquired scan data.

2. The apparatus of claim 1 wherein the fixture is optically coupled to the sample path through an optical fiber.

3. The apparatus of claim 1 wherein the fixture further comprises a camera that images some portion of the scanned area.

4. The apparatus of claim 1 wherein the fixture is adjustable to fit an arch shape of the teeth of a patient.

5. The apparatus of claim 1 wherein the source of low coherence light is a super-luminescent diode.

6. The apparatus of claim 1 wherein the interferometer is a Mach-Zehnder interferometer.

7. The apparatus of claim 1 wherein the interferometer is a Michelson interferometer.

8. The apparatus of claim 1 wherein the fixture is configured to scan one or more teeth or a full dental arch.

9. The apparatus of claim 1 wherein the actuator is a motor and the translation apparatus pulls the one or more scanners along the track under tension.

10. The apparatus of claim 1 wherein the control logic processor reconstructs 3D image data from scans of the teeth.

11. The apparatus of claim 1 wherein the translation apparatus urges the scanners in both directions along the curved scan path.

12. The apparatus of claim 1 wherein the scanner comprises a micro-electromechanical systems device.

13. The apparatus of claim 1 wherein the scanner comprises a motor driving a rotatable mirror.

14. The apparatus of claim 1 wherein the scanner comprises a gradient index lens.

15. An intraoral scanning apparatus comprising:
   a) a source of low coherence light;
   b) an interferometer that directs the low coherence light to a reference path and a sample path and that generates image data according interference from combined light returned along the reference and sample paths;
   c) a fixture that is optically coupled to the sample path, wherein the fixture comprises:
      (i) a bite portion featured for clamping between the jaws of a patient;
      (ii) a track that defines a curved scan path for scanning;
      (iii) a set comprising a plurality of scanners configured to simultaneously direct the sample path light to and from multiple sides of the teeth while scanning in a direction orthogonal to the curved scan path and absent lateral movement of the scanners relative to the track at locations along the curved scan path;
      (iv) an actuator and translation apparatus that urge the set of scanners along the curved scan path;
   d) a control logic processor that synchronizes light scanning and acquisition from the fixture; and e) a display in signal communication with the control logic processor for display of acquired scan data.

16. The apparatus of claim 15 wherein the fixture scans one or both dental arches in a single pass.

17. A method for intraoral scanning, the method executed at least in part by a computer and comprising:
   a) energizing a source of low coherence light;
   b) directing the low coherence light to a reference path and a sample path and generating image data according to interference from combined light returned along the reference and sample paths;
   c) optically coupling a fixture to the sample path, wherein the fixture comprises:
      (i) a bite portion featured for clamping between the teeth of a patient;
      (ii) a track that defines a curved scan path for scanning;
      (iii) one or more scanners configured to direct the sample path light to and from the teeth, wherein at least one scanner is operable to scan multiple surfaces of teeth at locations along the curved scan path absent lateral movement of the at least one scanner relative to the track;
      (iv) an actuator and translation apparatus that urges the one or more scanners along the curved scan path;
   d) synchronizing light scanning and acquisition from the fixture; and
   e) displaying, storing, or transmitting the acquired scan data.

* * * * *